United States Patent
Frieze et al.

(10) Patent No.: US 6,468,482 B1
(45) Date of Patent: Oct. 22, 2002

(54) FILTERED GAS PLASMA STERILIZATION CONTAINER WITH IMPROVED CIRCULATION

(75) Inventors: Marcia A. Frieze, Alpine; Allan S. Frieze, Apline, both of NJ (US); Kate Kislevitz, Westport, CT (US)

(73) Assignee: Case Medical, Inc., Ridgefield, NJ (US)

( * ) Notice: Subject to any disclaimer, the term of this patent is extended or adjusted under 35 U.S.C. 154(b) by 0 days.

(21) Appl. No.: 09/622,150

(22) PCT Filed: Apr. 8, 1999

(86) PCT No.: PCT/US99/08049

§ 371 (c)(1),
(2), (4) Date: Oct. 2, 2000

(87) PCT Pub. No.: WO00/12141

PCT Pub. Date: Mar. 9, 2000

Related U.S. Application Data

(63) Continuation-in-part of application No. 09/023,055, filed on Feb. 12, 1998, now Pat. No. 5,968,459, and a continuation-in-part of application No. PCT/US98/17671, filed on Aug. 26, 1998.

(51) Int. Cl.[7] .................................................. A61L 2/00
(52) U.S. Cl. ...................... 422/300; 206/363; 206/370; 422/297
(58) Field of Search .................. 422/297, 300; 206/363, 370

(56) References Cited

U.S. PATENT DOCUMENTS

| | | | |
|---|---|---|---|
| 4,748,003 A | | 5/1988 | Riley |
| 5,097,865 A | | 3/1992 | Riley |
| 5,340,551 A | * | 8/1994 | Berry, Jr. ..................... 422/300 |
| 5,384,103 A | | 1/1995 | Miller |
| 5,492,671 A | * | 2/1996 | Krafft .......................... 422/26 |
| 5,540,901 A | | 7/1996 | Riley |
| 5,628,970 A | | 5/1997 | Basile et al. |
| 5,681,539 A | | 10/1997 | Riley |
| 5,968,459 A | | 10/1999 | Nalepa et al. |

* cited by examiner

Primary Examiner—Krisanne Thornton

(57) ABSTRACT

A flash sterilization container (10) comprises a pan (12) forming the bottom of the container holding a tray (14), with a cover (16) forming the top of the container, and a filter element (20). Items to be sterilized are placed on the tray (14) and the cover (16) is attached and sealed to the pan (12). The sealed container is then placed in an autoclave or other source of pressurized steam. Items which require "stat" sterilization can be placed in a basket (80) with a plurality of vent holes (83) which further limits the amount, and therefore the whole mass, of the instruments placed into the container for sterilization and significantly decreases the time required for sterilization. The filter (20) allows the steam to enter the interior of the container and sterilize any items contained therein.

2 Claims, 15 Drawing Sheets

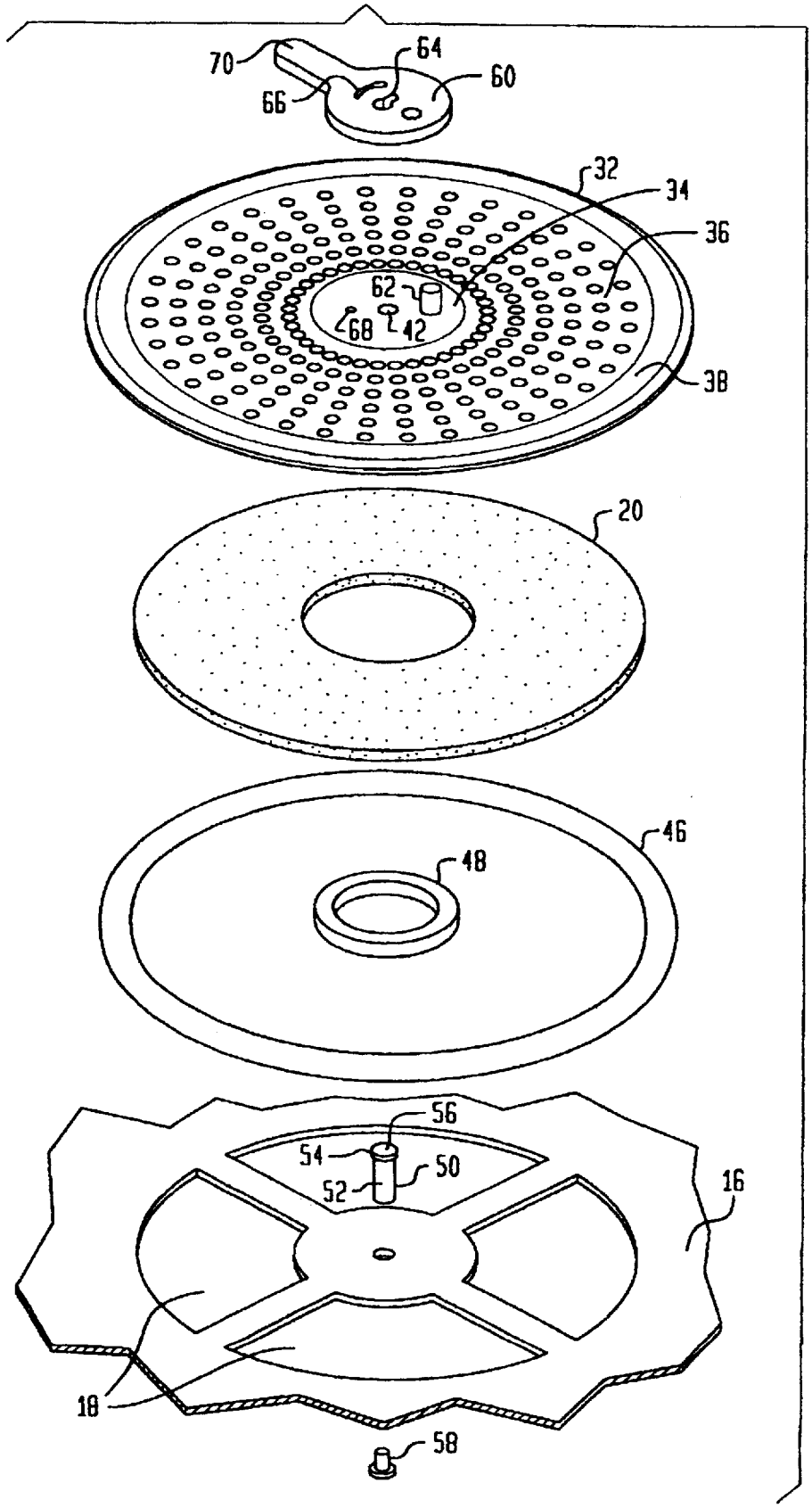

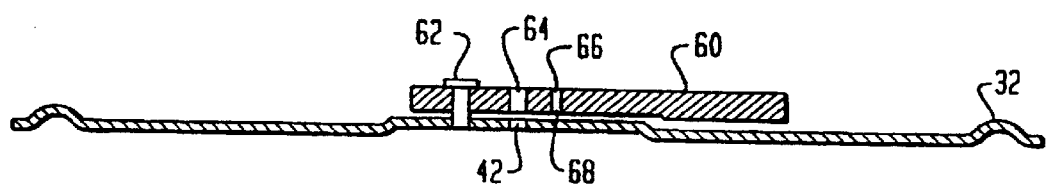
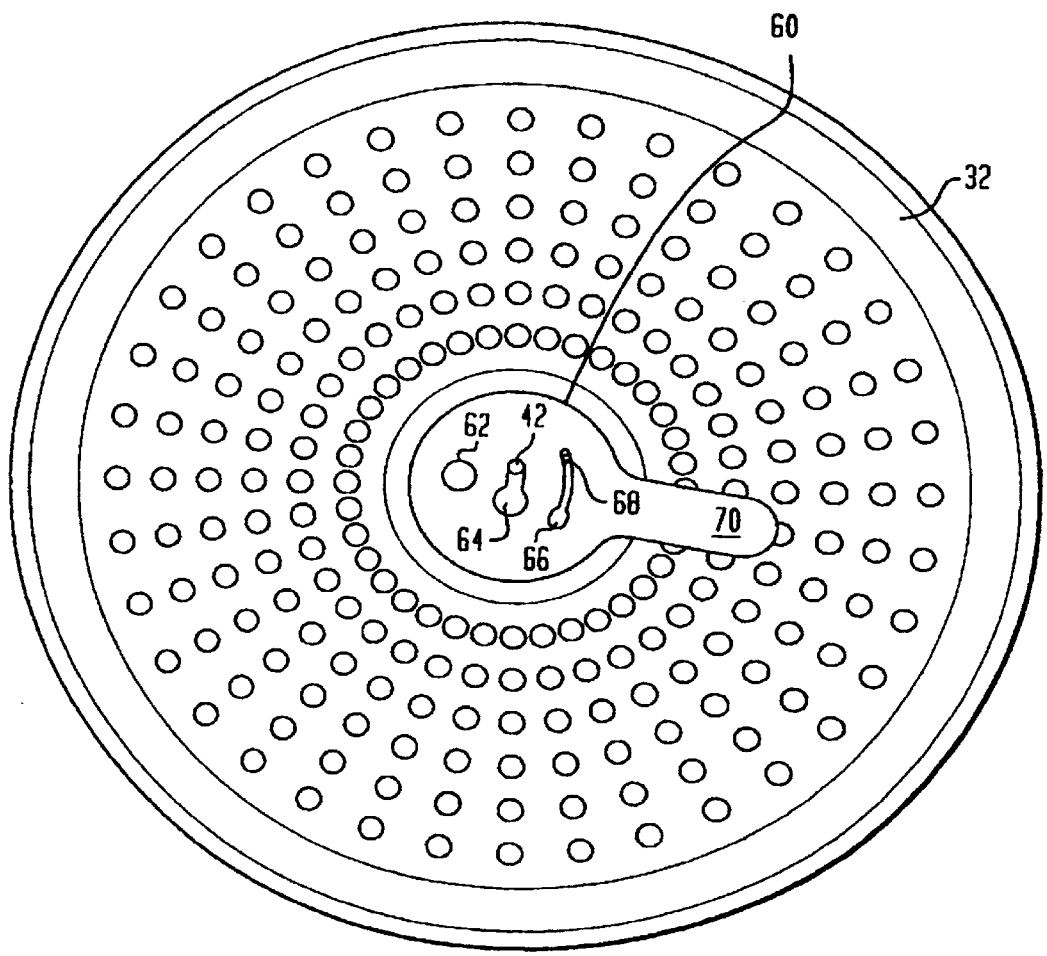

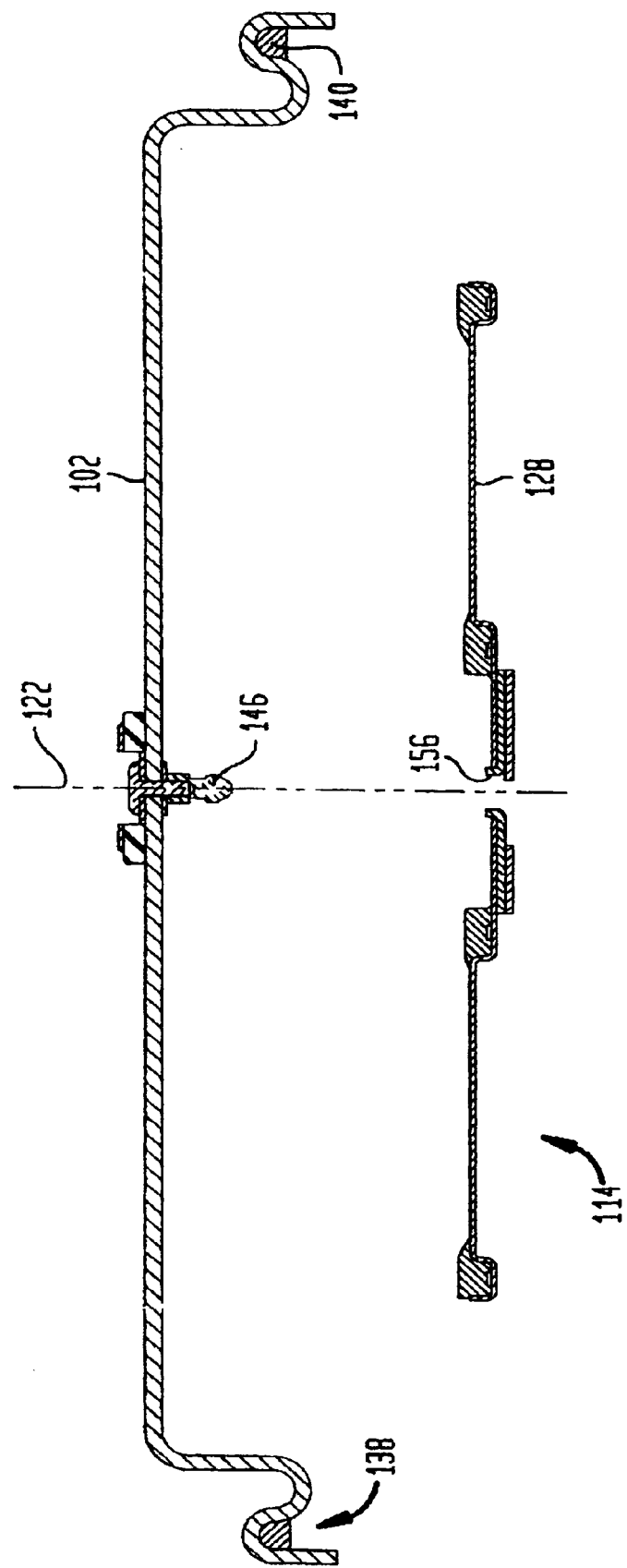

FILTERED GAS PLASMA STERILIZATION CONTAINER WITH IMPROVED CIRCULATION

CROSS REFERENCE TO RELATED APPLICATIONS

This application is a continuation-in-part of our co-pending U.S. application Ser. No. 09/023,055 filed on Feb. 12, 1998 now U.S. Pat. No. 5,968,459, entitled "Filtered Flash Sterilization Apparatus", issued on Oct. 19, 1999, and a continuation-in-part of our co-pending PCT application no. PCT/US/98/17671 filed on Aug. 26, 1998, the entire contents and substance of which are hereby incorporated by reference.

BACKGROUND OF THE INVENTION

1. Field of the Invention

The invention relates, in general, to a method for sterilizing medical instruments with steam and, in particular, to a sterilization container useful for flash sterilization and gas plasma sterilization, which includes a filter that permits maximum steam or gas sterilant penetration and prevents microorganisms and dust from entering, and which permits for stat flash sterilization by restricting the volume, and therefore the mass, of instruments placed into the container by utilizing a basket which fits into the container.

2. Description of Related Art

Steam sterilization is a common method used for the sterilization of items, especially medical instruments by processing the items in an autoclave and exposing them to high-pressure steam. This method requires the wrapping of individual items, heating the items with steam and then waiting for a drying/cooling period. Often during surgical procedures commonly used instruments are needed on a "stat" basis, i.e., the instruments-need to be quickly sterilized after use or inadvertent contamination. Under such circumstances the standard autoclave method would take too long. An alternative sterilization method, which can be used under these circumstances, is known as flash sterilization. In flash sterilization metal instruments are not wrapped but are heated directly by the steam allowing sterilization in a reduced period of time. One drawback to the use of flash sterilization is the lack of a drying period. When the items are still moist and hot from sterilization, microorganisms and dust can contaminate the items when they are transported from the autoclave/sterilizer. Nevertheless, flash sterilization results in reduced exposure time.

Sterilization time can also be reduced by limiting the amount of instruments placed into the sterilization container. If too many instruments with too much mass are placed into the sterilization container, "stat" sterilization will not be effective. One method to restrict the amount of instruments placed into the sterilization container is to weigh the instruments. Weighing of instruments, however, can be time consuming in itself and difficult to control given the various sizes, shapes and odd surface areas of medical instruments.

One common design for containers for flash sterilization is described in U.S. Pat. Nos. 5,097,865 and 4,748,003. Such containers use valves which require greater than atmospheric pressures to open the valves and allow the high-pressure steam to enter the container but are closed under normal pressure conditions. This approach has a number of disadvantages. Such containers must be opened to allow the steam to escape, thus breaking the sterile field. Even if kept sealed, these containers cannot maintain the sterile field for longer than 24 hours. Also, the high temperature, high-pressure valves needed for this method are very complex and very expensive. In addition, such containers do not provide an indication as to whether or not the valve properly functioned to allow the high pressure steam to enter the container.

In addition to flash steam sterilization the industry is beginning to use gas plasma as an alternative. One commercially available gas plasma system is sold as STER-RAD® by Advanced Sterilization Products, a division of the Johnson & Johnson Company. Gas plasma has known advantages over steam sterilization, including sterilizing at a lower temperature than required for steam sterilization, which is beneficial when sterilizing temperature-sensitive devices. However, it has been learned that frequently the sterilizing gas plasma does not reach all important surfaces on the inside of the sterilization container, especially where long tubular instruments or cables are contained. Accordingly, there are believed to be very few, if any, sterilization containers approved for use with gas plasma, especially in the mid-size range. Clearly a technique is missing in the prior art to guarantee satisfactory circulation of gas plasma within a sterilization container, especially where it is critical to reach the edges and corners of the interior of the sterilization container and to penetrate internal components such as laparascopic guides and tubing. The present invention, however, maintains its efficacy when utilized with gas plasma as the sterilant.

SUMMARY OF THE INVENTION

Briefly described, the invention comprises a sterilization container and a flash sterilization method for sterilizing items, which allow for extended, sterile storage of the sterilized items. The flash sterilization method uses a sterilization container having a pan, a cover and one or more filters for preventing dust and microorganisms from entering the container and contaminating the sterilized items while still allowing steam or gas plasma in and out of the container during the sterilization process. These containers can be used in the flash sterilization process commonly used in surgical theaters. The filter can be permanently mounted in the container or can be removable for replacement with new or different types of filters. Removable filters will allow for the retrofitting of currently used containers with the filters so that new containers do not need to be purchased to take advantage of the filtered flash sterilization method of the present invention. The filter can be removably attached to the container, manufactured as an integral part of the container, or incorporated into a self-contained removable filter unit.

A filter is attached to the sterilization container through a filter retainer. The filter retainer has a plurality of steam penetration holes which can be of various sizes and shapes allowing sufficient steam to enter the container. The filter retainer also comprises one or more gaskets for maintaining a seal between the filter retainer and the sterilization container as well as a locking means for removably attaching the retainer to the container.

Another aspect of the present invention allows for instruments to be sterilized on a "stat" basis by utilizing a basket which limits the amount of instruments that can be placed into the container for sterilization. When instruments need to be sterilized on a "stat" basis, for example, because the instrument became contaminated during the surgical procedure and no other such instrument is available, the time required to sterilize the instrument can be drastically reduced by limiting the amount or volume of instruments sterilized through utilization of a size restricted basket containing the instruments which would fit into the sterilization container. This indirectly limits the total mass of instruments to be sterilized, which in turn, reduces the sterilization time.

Another alternative embodiment of the invention provides for a single set of vent holes in the center of the lid, or cover, of the container and two sets of vent holes, arranged in a circular fashion, located in the base of the pan or bottom of the container. The second and third sets of vent holes in the base are located on opposite sides of the minor axis center line of the base in such a way that they do not overlap. Gas plasma passing through the first set of vent holes in the lid is then forced to travel to the extremes of the container in order to be exhausted thereby guaranteeing that all parts of the tray or sterilizable instruments on the inside come into contact with the gas plasma as well as the edges and corners and interior of the container.

According to yet another embodiment of the invention, a pair of vent means, comprising a first and fourth set, are located in the lid in a manner similar to the way the second and third set of vent holes are located in the base. This also helps to guarantee thorough circulation of the gas plasma within the container. These two improvements are especially suited for use with mid-size sterilizable containers that employ gas plasma as the sterilizing agent. This invention, however, enhances the efficacy of all methods of sterilization, including steam sterilization and gas plasma sterilization. The first, second, third and fourth sets of vent holes are preferably each arranged in four concentric circles having the holes on their circumference. Other alternative, symmetrical patterns, like square, would also be acceptable. The keeper plate on the bottom of the container preferably includes a similar set of holes, but offset so that there can be no "strikethrough" of sharp objects through the filter underneath the series of vent holes but above the keeper plate.

These and other features of the invention may be more fully understood by reference to the following drawings.

BRIEF DESCRIPTION OF THE DRAWINGS

FIG. 2A is an exploded perspective view of the flash sterilization container filter invention.

FIG. 3A is a side elevational view of the filter retainer invention.

FIG. 3B is a top plan view of the filter retainer invention with the locking means in the locked position.

FIG. 5E is a detailed, cross-sectional end view of the lid of FIG. 5B illustrated in a manner in which the snap-on post attaches to the filter retainer plate.

DETAILED DESCRIPTION OF THE INVENTION

During the course of this description like numbers will be used to identify like elements according to the different figures that illustrate the invention.

Figure 1A:
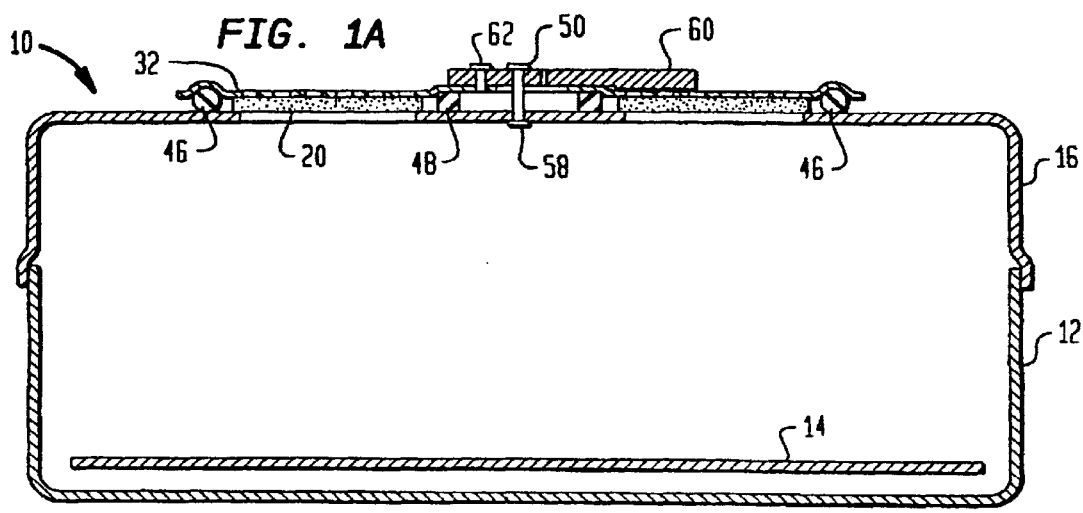
FIG. 1A is a perspective view of the flash sterilization container invention.
Figure 1B:
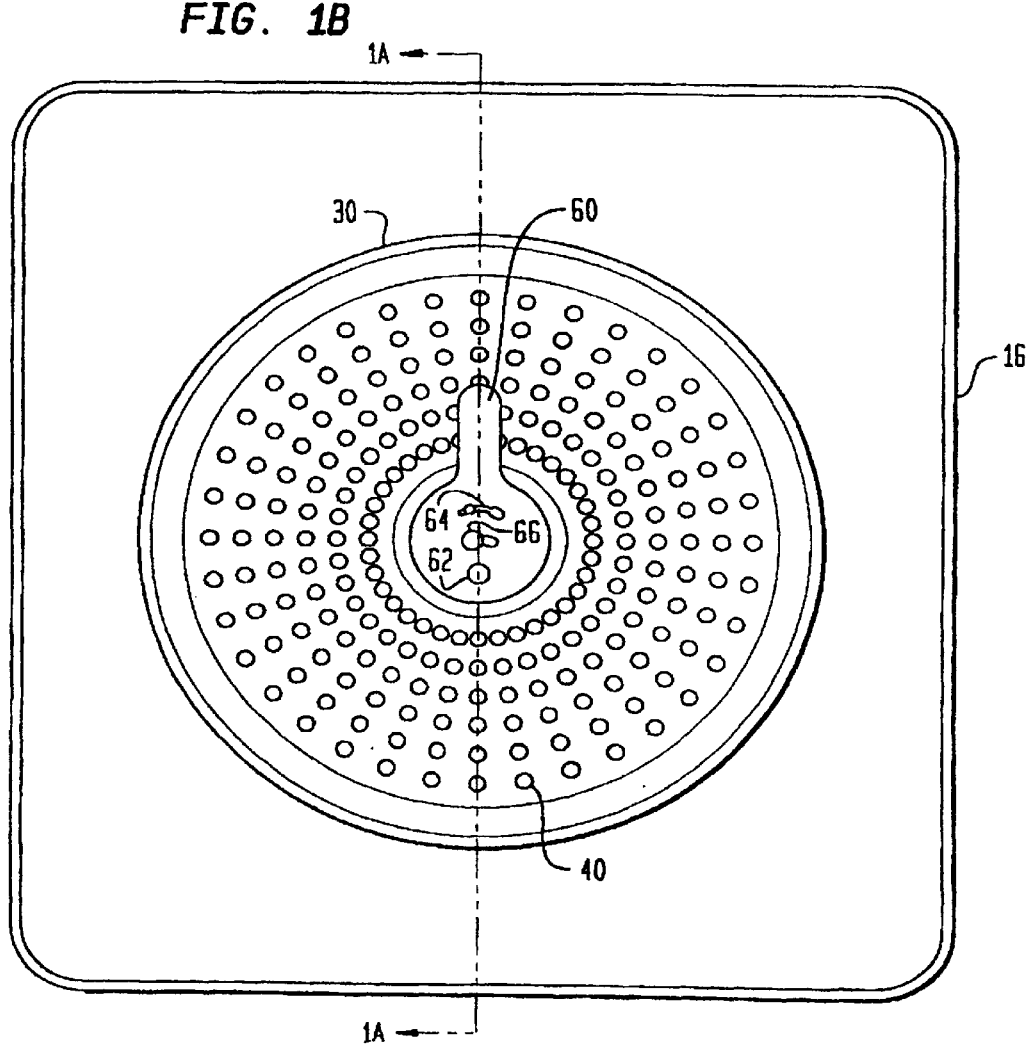
FIG. 1B is a top perspective view of the flash sterilization container cover with a filter retainer.
Figure 1C:
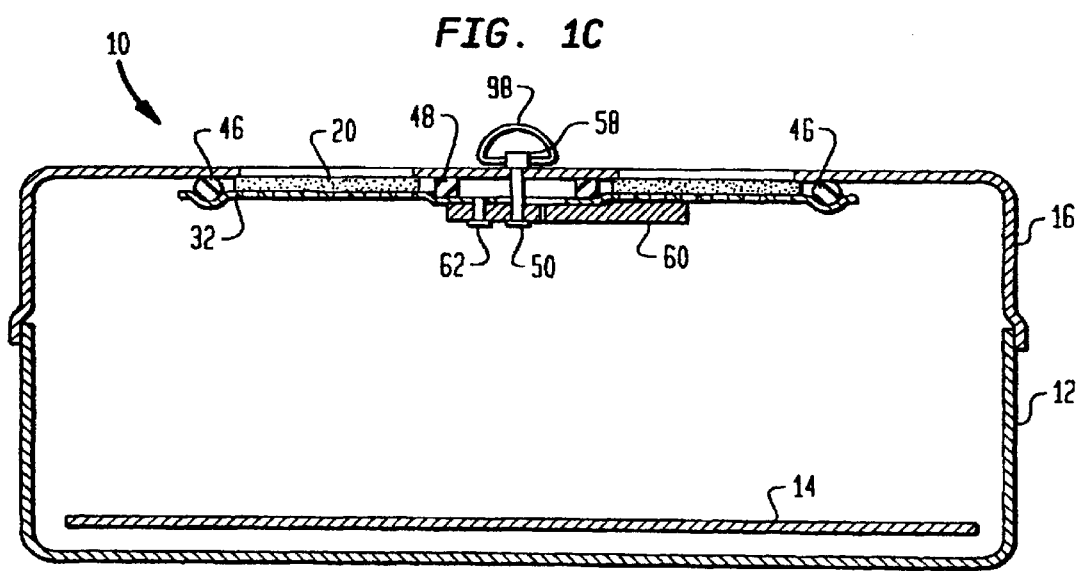
FIG. 1C is a perspective view of the flash sterilization container invention with the top surface of the lid having a D-ring attached to it.
Figure 2B:
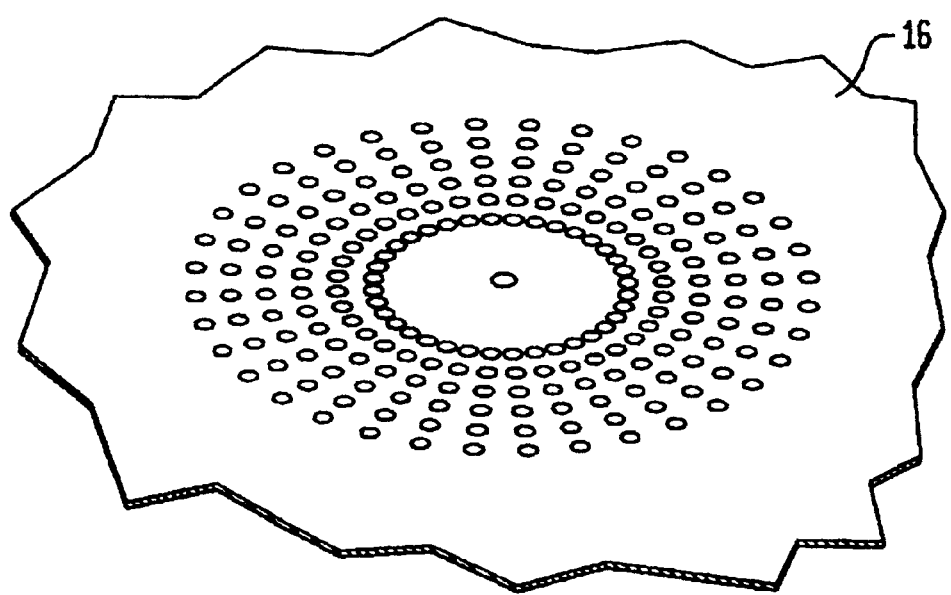
FIG. 2B is a partial view of a cover opening configuration.
Figure 3C:
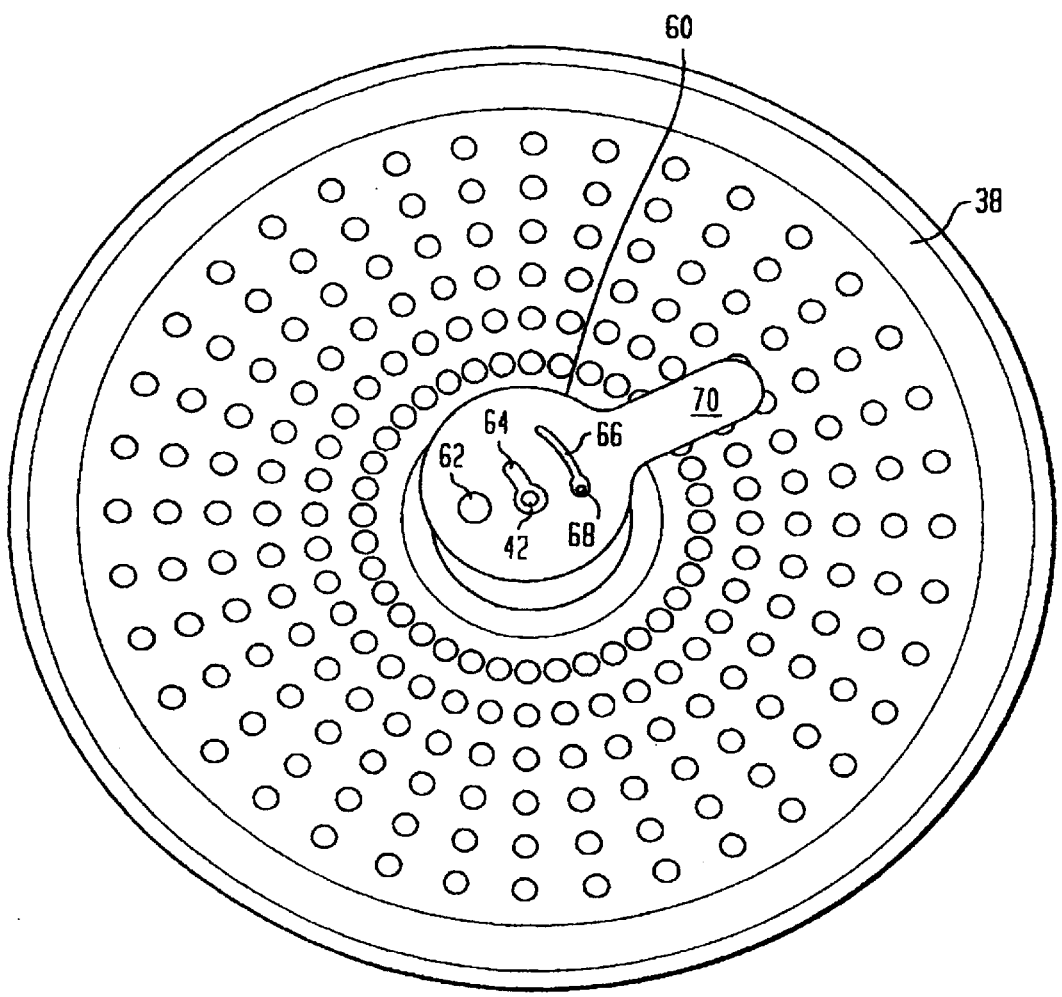
FIG. 3C is a top plan view of the filter retainer invention with the locking means in the unlocked position.

The flash sterilization container invention 10 is illustrated in FIG. 1. A sterilization container 10 comprises a pan 12, which forms the bottom of the container that holds and supports a conventional sterilizable tray 14, and a cover 16, which forms the top of the container. The cover is removably attached to the pan to form a hermetically sealed container. This can be accomplished by conventional means such as hinges and clamps and a sealing gasket. The cover 16 is provided with an opening 18 at its top. This opening 18 is covered with a filter 20 to allow steam to enter and exit the container through the opening by passing through the filter. The filter can be removably or permanently attached to the cover. This filter is made of a material, or combination of materials, such that the filter is permeable to the flow of steam but will inhibit dust or other airborne particles or microorganisms from passing through. Examples of such materials include paper, TEFLON®, a registered trademark of E.I. Du Pond de Nemours and Co., Inc., porous stainless steel, polysulfone, and hydrophobic material, such as GOR-TEX®, a registered trademark of W.L. Gore & Associates, and Kimguard®, a trademark of the Kimberly-Clark Corporation. The filter is attached to the cover by means which will prevent any steam, dust or other airborne particles or microorganisms from passing through the opening in the cover without passing through the filter.

The filter 20 is placed over the opening 18 in the top of the cover 16 and the filter is attached to the cover by a filter retainer 30. One embodiment of such a filter retainer is illustrated in FIGS. 1A, 1B, 2A, 3A and 3B. The filter retainer 30 comprises a filter retainer disc 32 and a means for sealing the filter retainer disc to the cover. The filter retainer disc has an inner disc 34, a middle ring 36, and an outer ring 38. The middle ring 36 has a plurality of holes 40 to allow the flow of steam through the filter retainer disc 32, through the filter 20, and through the opening 18 in the cover 16. The filter retainer can have one or more sealing means for forming a seal between the filter and the cover. The outer ring 38 has a means for forming a seal between the filter and the cover. In one embodiment the outer ring has an inverted-u shaped cross-section. A gasket 46 is placed in the inverted-U outer ring and can be made of silicone, neoprene, TEFLON®, a registered trademark of E.I. Du Pond de Nemours and Co., Inc., or any other suitable material. Inner disc 34 may also have a sealing means if necessary, such as a gasket 48.

A means for attaching the filter retainer to the cover is illustrated in FIGS. 1A, 1B, 2A, 3A, and 3B. Pin 50 extends upwards from the top surface of the cover 16. Inner disc 34 of the filter retainer disc 32 has a hole 42 for accepting pin 50. Pin 50 has sufficient length to extend past the top surface of the filter retainer 30 when the filter retainer is placed on the cover 16 allowing the hole in the inner disc 42 to engage the pin 50. Pin 50 is preferably located in the center of the opening 18 in the cover 16. To locate the pin in the proper position, the opening in the cover can be, for example, a circular opening with cross pieces such as those illustrated in FIG. 2A. In an alternate embodiment, the opening in the cover can be comprised of a multiplicity of smaller openings in the cover, as depicted in FIG. 2B. A locking means is located on the inner disc which engages the pin 50 and holds the filter retainer in place.

The preferred locking means is comprised of a sliding plate 60 which is movably attached to the inner disc 34 of the filter retainer disc 32 with a hinge pin 62 extending from the inner disc 34 of the filter retainer disc 32, so that the sliding plate 60 rotates about the center of the hinge pin 62 while remaining in contact with the inner disc. The sliding plate 60 has an arc-shaped pin slot 64 having an effective radius equal to the distance from the hinge pin 62 to the hole in the center of the inner disc 42, whereby the center of the hole in the inner disc maintains alignment with the center of the arc-shaped slot throughout the rotation of the sliding plate.

The retainer pin 50 is comprised of a cylindrical body 52 having opposite ends and an outside diameter essentially equal to the inside diameter of the hole 42 in the filter retainer disc, a cylindrical neck 54 having a diameter smaller than the diameter of the body and equal to the width of the arc shaped slot 64, and a cylindrical head 56 having a top and a bottom and having a diameter larger than the pin neck 54, preferably equal to the diameter of the pin body 52. One end of the pin body 52 is attached to the cover 16 by conventional means, such as, a rivet 58, a screw, a thread, or a spot weld. Pin neck 54 is attached to the end of the pin body 52 opposite the attachment to the cover. The bottom of the pin head is attached to the pin neck at the end opposite the pin neck's attachment to the pin body. The retainer pin can be made of separate elements attached by conventional means or preferably manufactured from a single piece of stock. The length of the pin body is essentially equal to the distance from the top surface of the cover to the top surface of the inner disc. The length of the pin neck is at least equal to the thickness of the sliding plate. The combined length of the pin body and pin neck is such that the bottom of the pin head is slightly lower than the top surface of the sliding plate 60 so that when the arc-shaped pin slot 64 engages the pin neck 54, the filter retainer disc 32 will be forced toward the cover, compressing the gaskets 46, 48, and creating a seal between the filter retainer 30 and the cover 16. The top of the pin head 56 can have a taper to facilitate the insertion of the retainer pin 50 through the hole in the filter retainer disc 42 and arc-shaped slot in the sliding plate 64.

The arc shaped slot 64 has a width essentially equal to the outside diameter of the pin neck and a length at least twice as long as the outside diameter of the pin head. At one end of the arc-shaped slot 64, the width of the slot is increased to allow the pin head to pass through the arc-shaped slot.

A filter is attached to the cover with the filter retainer by placing a filter 20 over the hole 18 in the cover 16, the sliding plate 60 is positioned so that the end of the arc-shaped slot 64 having an increased width is aligned with the hole in the inner disc 42, the filter retainer 30 is then placed over the opening in the cover 16 so that the retainer pin 50 passes through the hole in the inner disc 42 and the enlarged end of the arc-shaped slot 64, and the sliding plate 60 is then rotated so that the arc-shaped slot 64 engages the pin neck 54, thereby preventing the pin from passing back through the arc-shaped slot and thus attaching the filter retainer to the cover.

The filter retainer 30 has a means for limiting the rotation of the sliding plate 60 and facilitating the positioning of the sliding plate in an "open" position, where the enlarged end of the arc-shaped slot 64 lines up with the hole in the inner disc 42, and a "locked" position, where the opposite end of the arc-shaped slot lines up with the hole in the inner disc. One embodiment of a limiting means incorporates an arc-shaped limiting slot 66 on the sliding plate 60. The arc of the limiting slot 66 is parallel to the arc of the arc-shaped slot 64 and has an effective radius larger than the radius of the arc-shaped slot 64. A locating pin 68 is attached to, and extends from, the inner disc 34 such that it engages one end of the limiting slot 66 when the sliding plate 60 is in the locked position and engages the opposite end of the arc-shaped slot when the sliding plate is in the unlocked position. The locating pin 68 is preferably hemispherical-shaped to facilitate the movement of the sliding plate 60 over the locating pin 68. A hemispherical locating pin 68 can be made, for example, by inserting and attaching a ball bearing in a hole in the inner disc 34. The width of the limiting slot 66 is slightly less than the diameter of the locating pin 68. The width of the limiting slot 66 at each of the two, opposite ends, is enlarged slightly, forming two holes each having a diameter slightly larger than the diameter of the locating pin 68. Consequently, the sliding plate 60 is held in the locked and open positions when the locating pin 68 engages each of the holes in the ends of the limiting slot 66, requiring the application of an external force to move the sliding plate between the two positions.

The sliding plate 60 preferably has a handle 70 to facilitate moving the plate between the open and closed positions. The handle 70 preferably extends parallel to the plane of the sliding plate. The handle 70 can be attached to the sliding plate or manufactured with the sliding plate as a single piece.

Figure 4A:
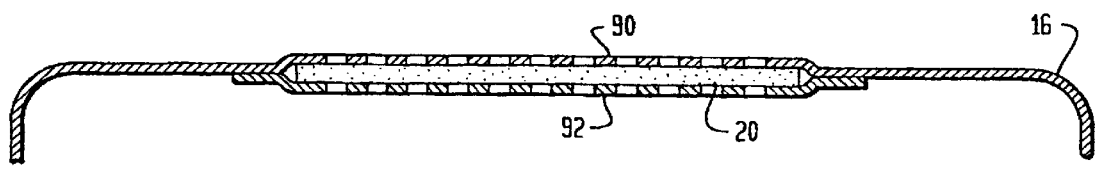
FIG. 4A is a partial, side elevational view of a flash sterilization container cover with an incorporated filter.
Figure 4B:
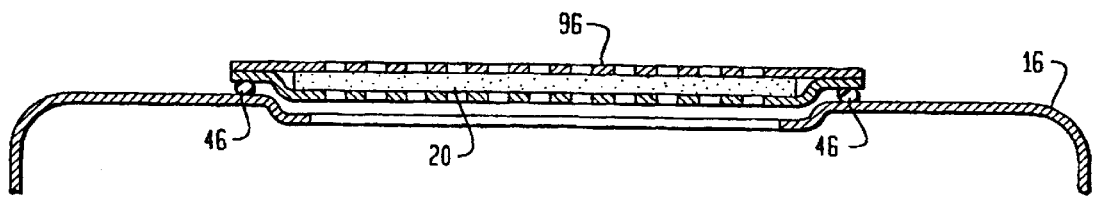
FIG. 4B is a partial, side elevational view of a flash sterilization container and a filter cartridge.

As described above, the sterilization container has a filter retainer mechanism. Alternative embodiments comprise having the filter manufactured as an integral part of the container as depicted in FIG. 4A, or having the filter incorporated into a self-contained removable filter unit or cartridge as depicted in FIG. 4B.

A further alternative embodiment comprises a D-ring attached to the end of pin 50 connected to the cover 16. In this embodiment, the filter and filter retainer are mounted on the inside of the sterilization container. This arrangement permits the external D-ring to be used as a handle to lift the cover without coming into contact with the side edges of the cover 16, thereby reducing the risk of contamination of the container contents.

While the foregoing embodiment works sufficiently well in a flash sterilization environment, it has been found that improvements to the basic structure of the invention are desirable if used with gas plasma. Gas plasma as a sterilization medium is fairly new and is available from, among others, Advanced Sterilization Products, a division of Johnson & Johnson, under the trademark STERRAD®. Gas plasma has certain advantages over the prior art. For example, ethylene oxide has been banned thereby making it more difficult to find suitable alternatives. In addition, steam sterilization cannot be used with a number of modem tools, such as cannulas, lumens, scopes, fiber optic cables, and cameras, without damaging them. While gas plasma clearly has certain distinct advantages, it has been found that it does not operate suitably well with all types of containers that were suitable for use with steam sterilization. Part of the problem is that the gas plasma does not circulate as aggressively as steam inside the container, and does not reach areas such as the comers, thereby leaving the potential for unsterilized surgical instruments or the like. Steam sterilization avoids the absorption problem by having a super-saturated environment of water molecules. The present invention, however, has provided a way for making gas plasma acceptable for use in sterilization containers, especially those in the mid-size range. For the purposes of this disclosure, mid-size is defined as approximately 15–18" in length, 9–12" in width and 2–10" in depth. The container, especially in the mid-size container, has several advantages, including but not limited to, the following: 1) it cuts the exposure time in steam sterilization; 2) it improves the effectiveness of gas plasma sterilization; and 3) it is more efficacious for gravity displacement applications.

Figure 5A:
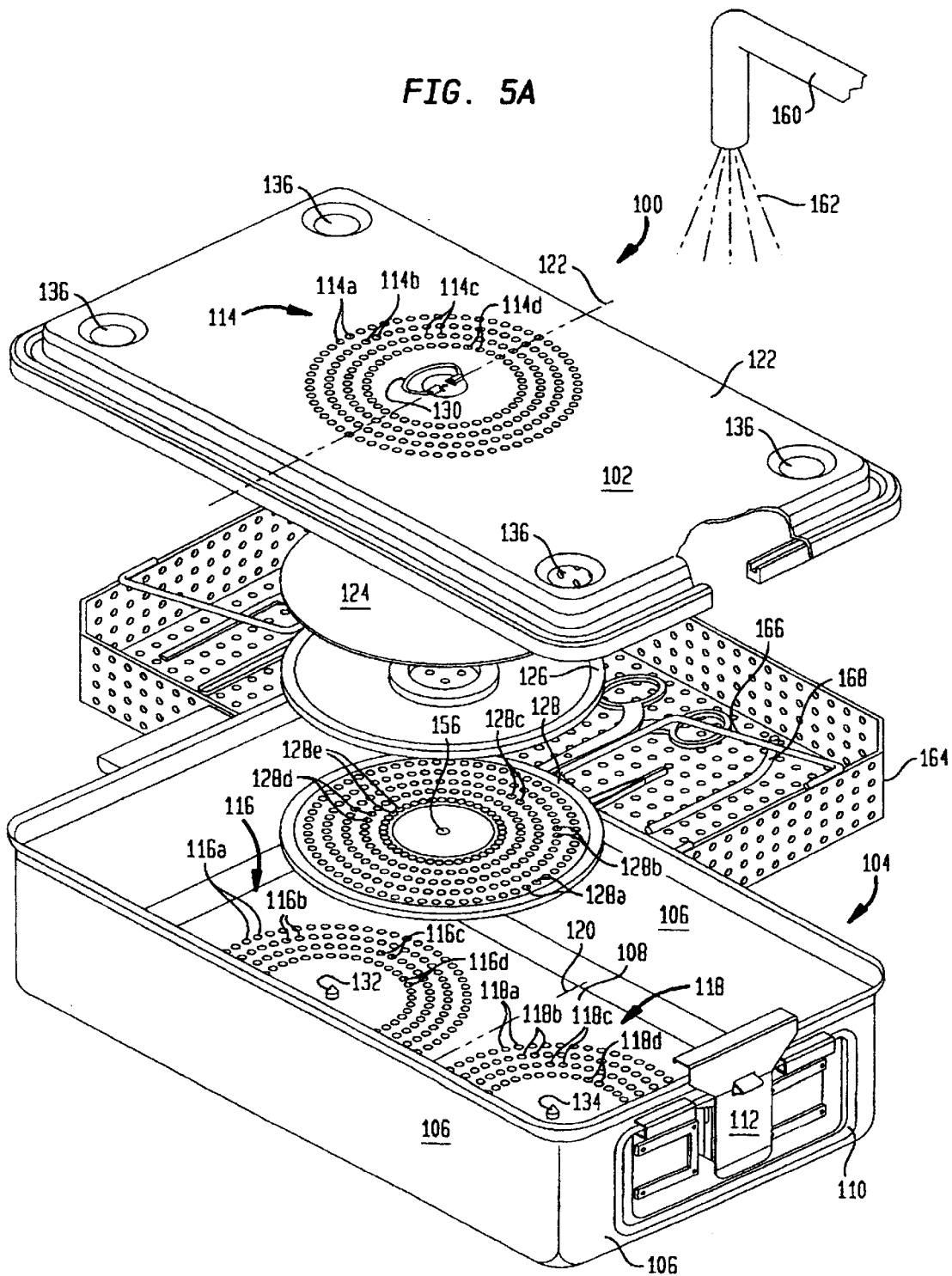
FIG. 5A is an exploded view of an alternative embodiment of the invention especially suitable for use with gas plasma in which the base of the container includes two sets of circular vent holes located on opposite sides of the center line of the minor axis of the container.
Figure 5B:
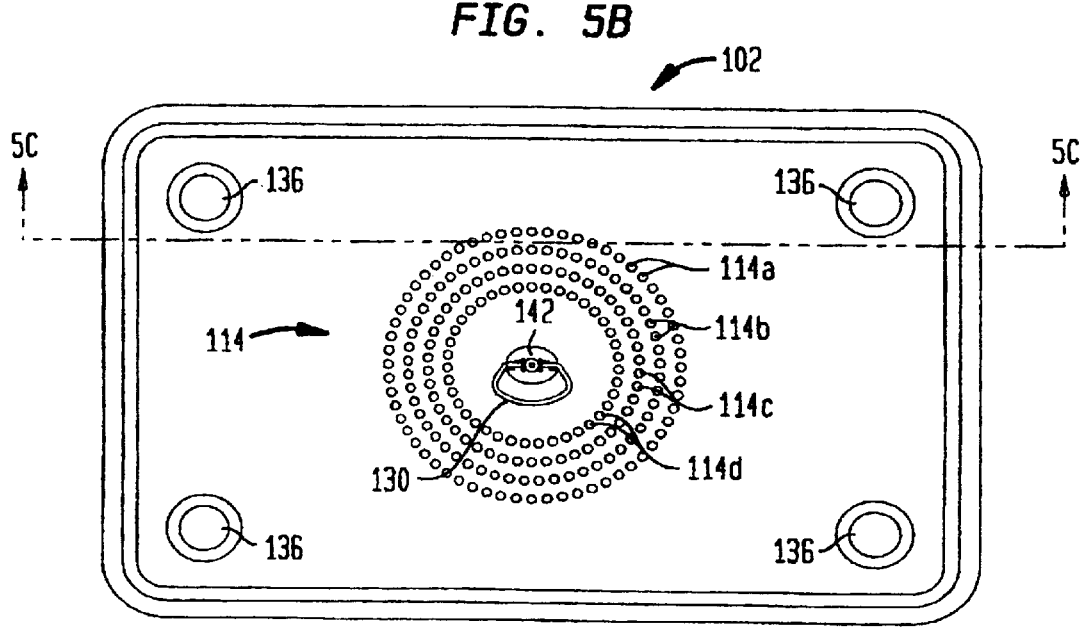
FIG. 5B is a top plan view of the lid of the alternative embodiment illustrated in FIG. 5A.

A first alternative embodiment 100 of the improved gas plasma sterilization container apparatus is illustrated in the exploded view of FIG. 5A. The container 100 includes a top or lid 102 that sits on top of a bottom or pan 104. Bottom 104 includes four sidewalls 106 and a bottom or base 108. A pair of wire handles or bales 110 are located on opposite ends of the bottom portion 104 and are held in place by a pair of lockable latches 112.

A first set of vent holes 114 is located in top 102. The vent holes 114 are preferably arranged as a group of four concentric circles with holes 114a, 114b, 114c and 114d in each, respectively. In all, the total number of holes may range from 100 to 500 and have a size that ranges in diameter from, but not limited to, ³⁄₁₆' to ⁵⁄₁₆'. The first set of vent holes 114 is located on the central axis 122 of the short dimension of the lid 102. The first set of vent holes 114 allows the sterilizing medium 162 to pass into the container. A pull ring 130, attached to a base 142 sits in the middle of the first set of vent holes 114 and is connected there by rivet assembly 144a, 144b, and 144c as shown in exploded detail in FIG. 5D. The lid 102 also includes four recessed dimples 136 which are adapted to engage with complimentary dimples or projections in the base 108 (not shown) so that the containers 100 can be stacked on each other and permit circulation of gas plasma therethrough at the same time.

Figure 5C:
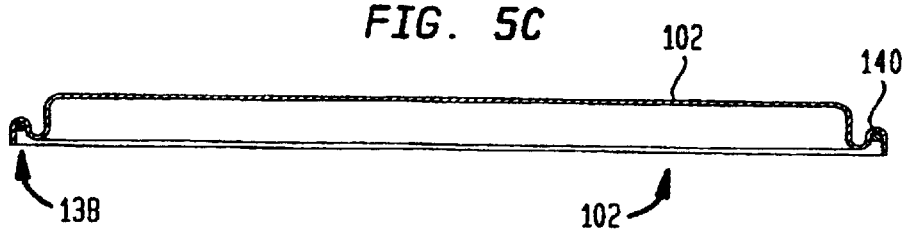
FIG. 5C is an elevational cross-sectional view of the lid illustrated in FIG. 5B.
Figure 5D:
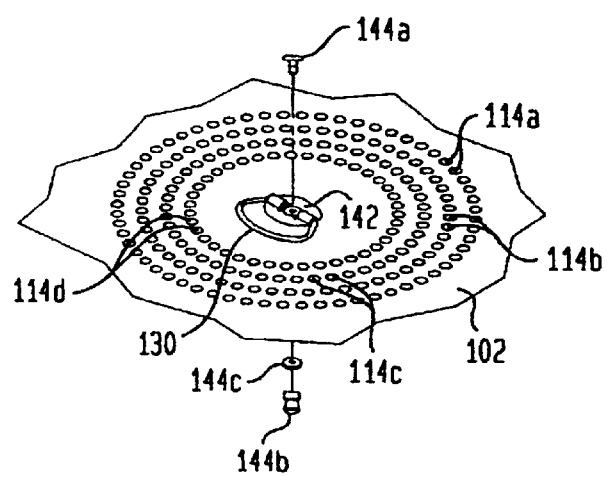
FIG. 5D is a partial, cross-sectional exploded view of the top, or first set, of circular vent means illustrated in a manner in which the pull ring is attached to the lid.
Figure 5F:
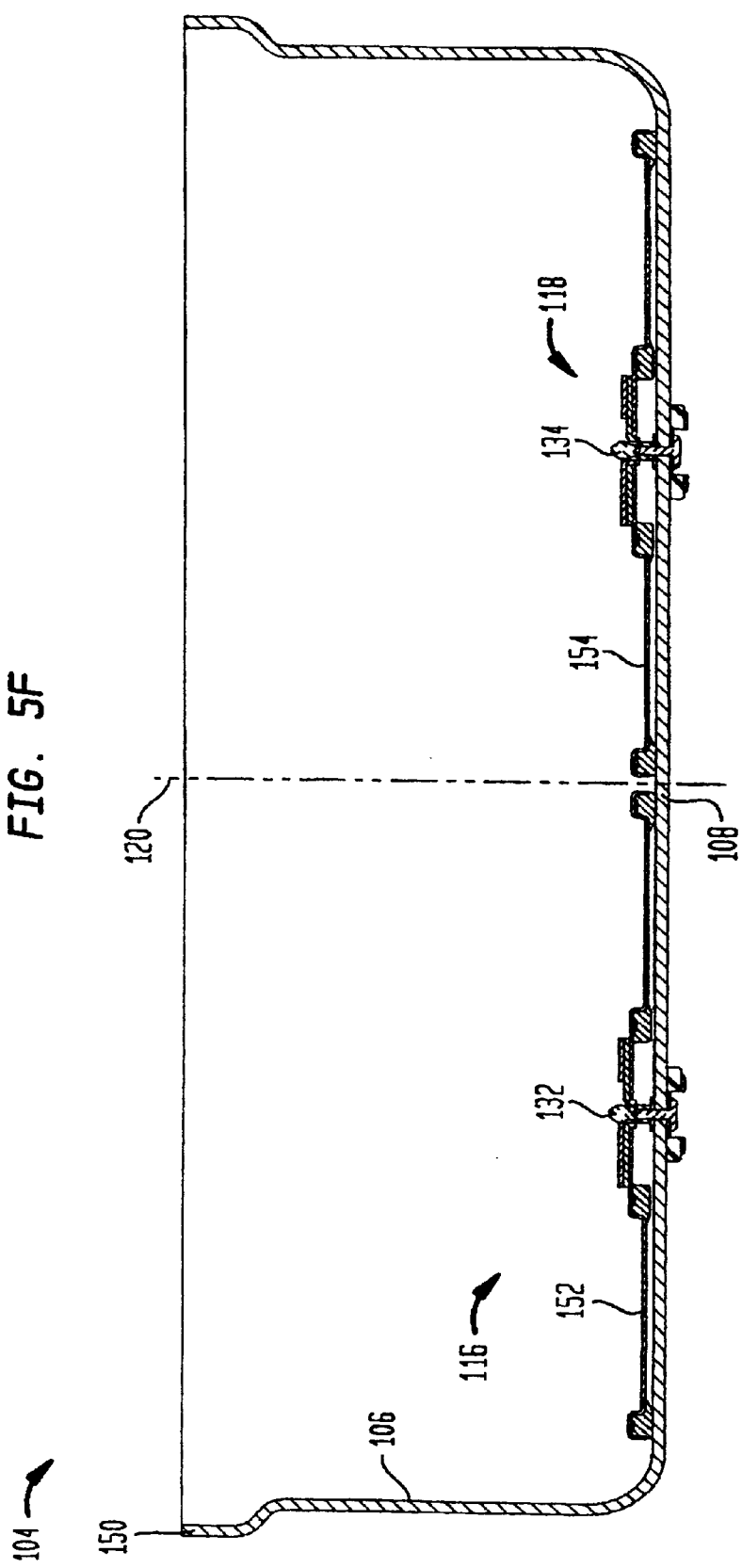
FIG. 5F illustrates the bottom, or pan, of the gas plasma alternative embodiment illustrating how the second and third set of circular vent means are located on opposite sides of the center line of the minor axis of the bottom portion.

A second set of vent holes 116 and a third set of vent holes 118 are located in the base 108 on symmetrical opposite sides of center line 120 which represents the minor axis of the base 108. The second set of vent holes 116 also comprises four concentric circles having holes 116a, 116b, 116c and 116d of the same dimensions with regard to the first set of vent holes 114. A hold-down stud 132 is located in the center of the concentric circles and is intended to make a snap fit with the retainer plate for the hydrophobic filter that goes therebetween. Similarly, the third set of vent holes 118 comprises four sets of concentric circles having holes 118a, 118b, 118c and 118d therein. A central post or stud 134 is also located in the middle thereof and adapted to snap into and engage a hydrophobic filter retainer plate in the manner previously described with regard to the flash sterilization embodiment. Associated with the first set of vent holes 114 is a circular hydrophobic filter disk 124, a hold down ring 126 and a perforated filter retainer plate 128. A central hole 156 in the retainer plate 128 snaps into and engages a stud 146 in the container as illustrated in FIG. 5E. A similar set of hydrophobic filters, rings, and retainer plates is associated with the second and third set of vent holes 116 and 118 as illustrated in FIG. 5F. Hydrophobic filters 124 should be utilized when gas plasma acts as the sterilizing medium, whereas cellulosic filters can be used when steam or ethylene oxide acts as the sterilizing medium. The TYVEK®, a trademark of E.I. du Pont de Nemours & Company, brand of polyethylene/polypropylene spun fiber is acceptable, as is Kimguard®, a trademark of the Kimberly-Clark Corporation. The alternative embodiments 100 and 200 also work best with hydrophobic filters such as described above. In addition, hydrophobic filters do not absorb water, which allows for a quicker drying time. The concentric holes 128a, 128b, 128c, 128d and 128e, are preferably offset from the holes 114a, 114b, 114c, and 114d so as to the prevent "strikethrough". That is to prevent sharp objects from entering the holes 114a, 114b, 114c and 114d and exiting through 128a, 128b, 128c, 128d or 128e. As illustrated in FIG. 5C the top or lid 102 includes a groove 138 which retains a gasket 140 which sits on top of the upper lip 150 of the bottom or base pan 104 as shown in FIG. 5F. FIG. 5F also shows in further detail how the bottom perforated retainer plate 152 attaches to the bottom stud 132 and keeps a hydrophobic filter in place above the second set of vent holes 116. Similarly, FIG. 5F also illustrates how another perforated filter retainer plate 154 engages snap on stud 134 to hold another hydrophobic filter in place above the third set of perforated vent holes 118.

The structure just described works especially well with gravity displacement or gas plasma. The gas plasma enters through the vent holes 114, passes through the hydrophobic filter 124 and emerges through the perforated base plate 128. Because the top vent holes 114 are not located directly above the bottom pair of vent holes 116 and 118, the gas plasma is forced to migrate, and become somewhat turbulent as it attempts to find an exit through the second and third set of circular vent holes 116 and 118, respectively. This forces the gas plasma to more thoroughly mix and contact medical instruments or the like inside of the container 100 and also forces it further towards the corners and edges of the container. As a consequence, the invention described is one of a few containers, if any, that has been approved by major manufacturers for use with gas plasma. It is believed that no sealed container in the mid-size range for sterilization of blades and cannulas has been approved at the present time. The present invention in the mid-size range with the offset sets of vent holes works in all methods of sterilization, including flash sterilization, steam sterilization, and gas plasma sterilization.

Figure 6A:
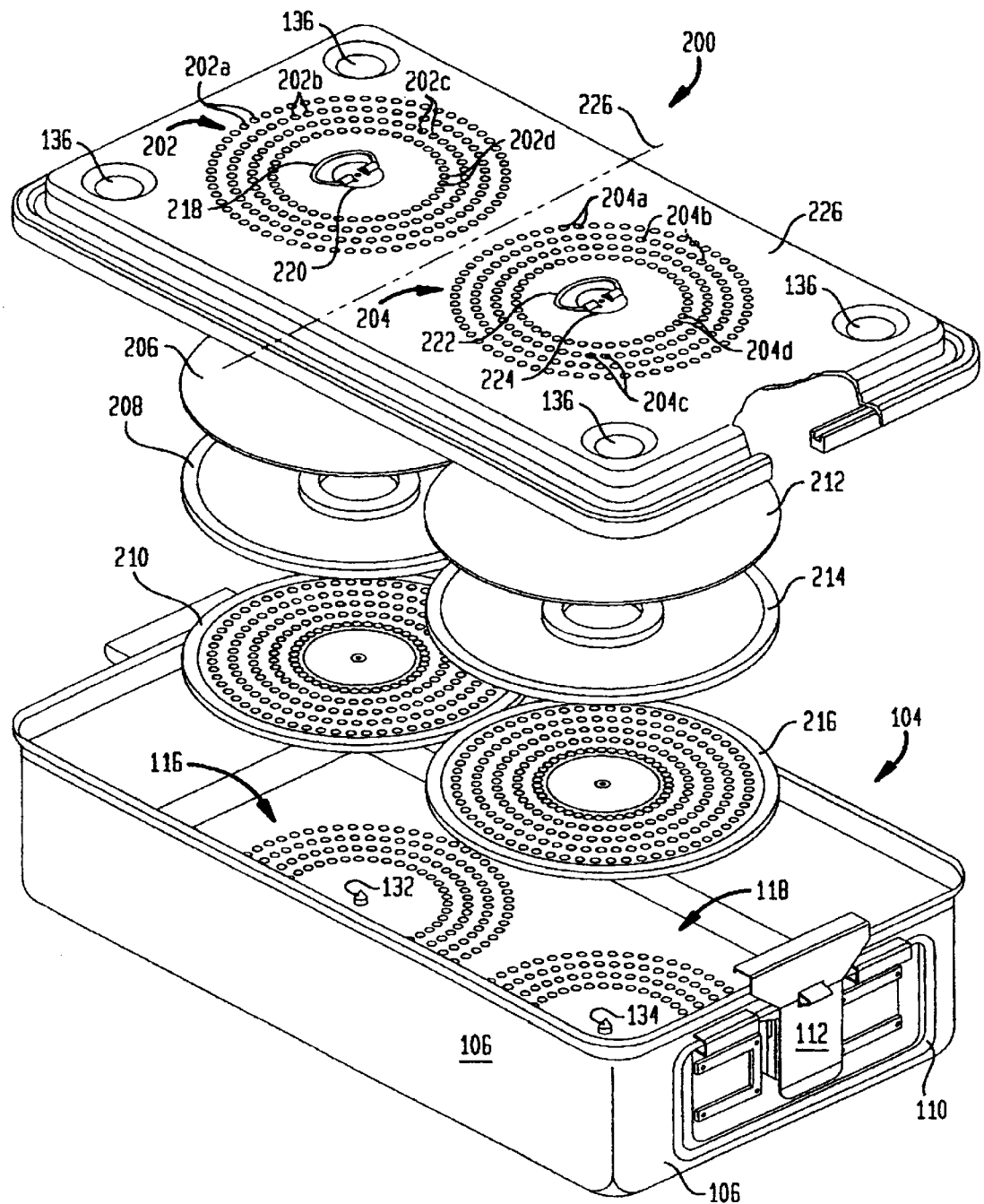
FIG. 6A is an exploded view of another alternative embodiment of the gas plasma container illustrating a fourth set of circular vent means located adjacent to said first set of circular vent means in the top of lid of the container.
Figure 6B:
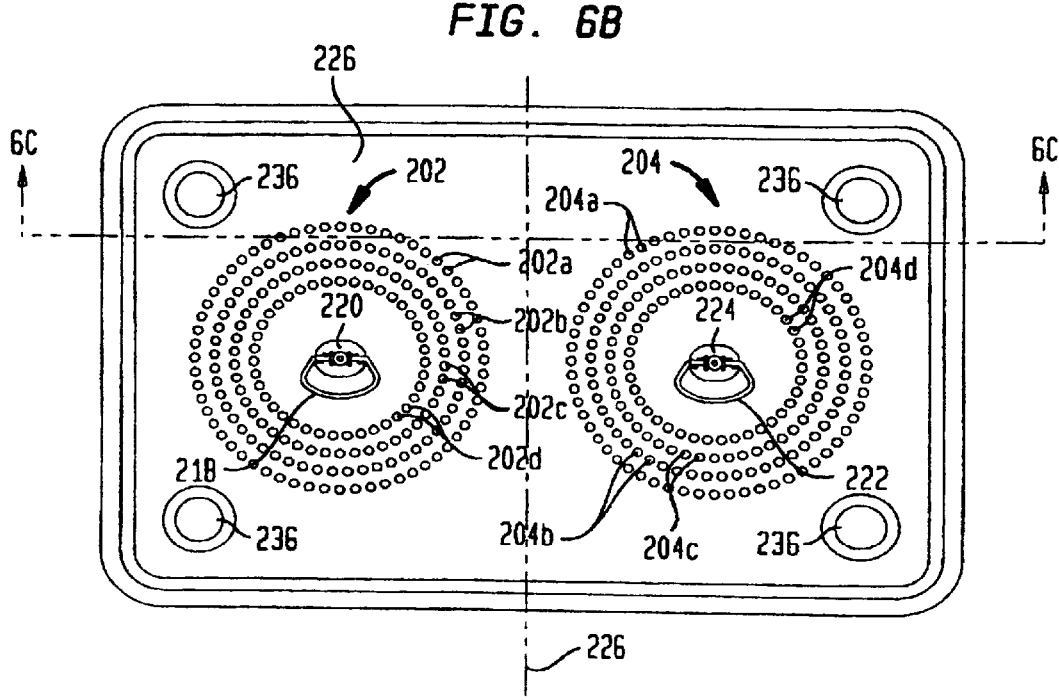
FIG. 6B is a top plan view of the lid of the alternative embodiment illustrated in FIG. 6A.
Figure 6C:
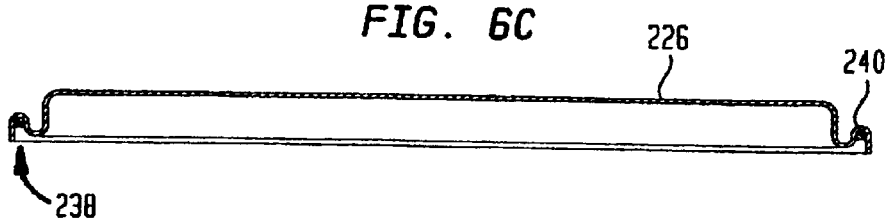
FIG. 6C is a side elevational cross-sectional view of the lid illustrated in FIG. 6B.
Figure 6D:
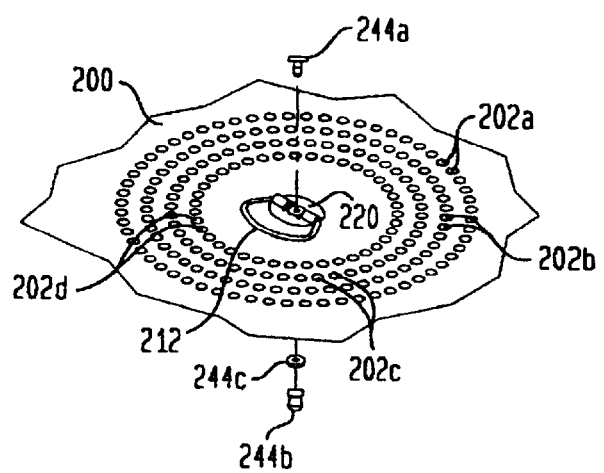
FIG. 6D is a partial, detail exploded view of the first set of circular vent means illustrating the manner in which the pull ring is attached to the lid.

A second alternative embodiment 200 of the gas plasma version is illustrated in an exploded view shown in FIG. 6A. The base, or bottom pan 104 of the embodiment 200 is identical in all respects to the base 104 illustrated in FIG. 5A and associated with the first gas plasma alternative embodiment 100. Namely, the base 104 also includes a pair of offset circular vent holes 116 and 118 each having a hydrophobic filter and a retainer plate associated therewith as seen, for example, in detail in Fig. 5F. The difference between embodiment 100 and 200 is that alternative embodiment 200 includes a pair of circular sets of vent holes 202 and 204 arranged symmetrically on opposite sides of the small dimension center line 226. The structure of the first and second set of vent holes 202 and 204 is identical to the structure of the set of vent holes 114 in the lid 102 of embodiment 100 as illustrated in FIGS. 5A–5F. Namely, the first set of vent holes 202 comprises four concentric circles of vent holes 202a, 202b, 202c and 202d. A pull ring 218 connected to a base 220 is located in the center of the concentric circles 202. Pull ring 218 is attached by a rivet assembly 244a, 244b, and 244c as illustrated in exploded detail in FIG. 6D. Similarly, the second set of vent holes 204 comprises four concentric circles having vent holes 204a, 204b, 204c and 204d arranged around a pull ring 222 attached to a base 224 and connected to the lid 226 in the same manner as illustrated in FIG. 6D. The first set of vent holes 202 has associated with it a hydrophobic filter disk 206, a ring 208, and a perforated retainer plate 210 that snaps and attaches to a post on the bottom side of the base plate 220 in the same manner that the post 146 of the embodiment 100 engages its perforated retainer plate 128 as illustrated in FIG. 5E. Similarly, another hydrophobic filter disk 212 is located under the second set of vent holes 204, and has an associated ring 214 and perforated retainer plate 216 below it which also engages with a snap on post associated with pull ring 222 and base plate 224. This second alternative embodiment 200 also provides for improved circulation of the gas plasma through the container so as to contact all the surgical instruments and the corners of the device.

Figure 7A:
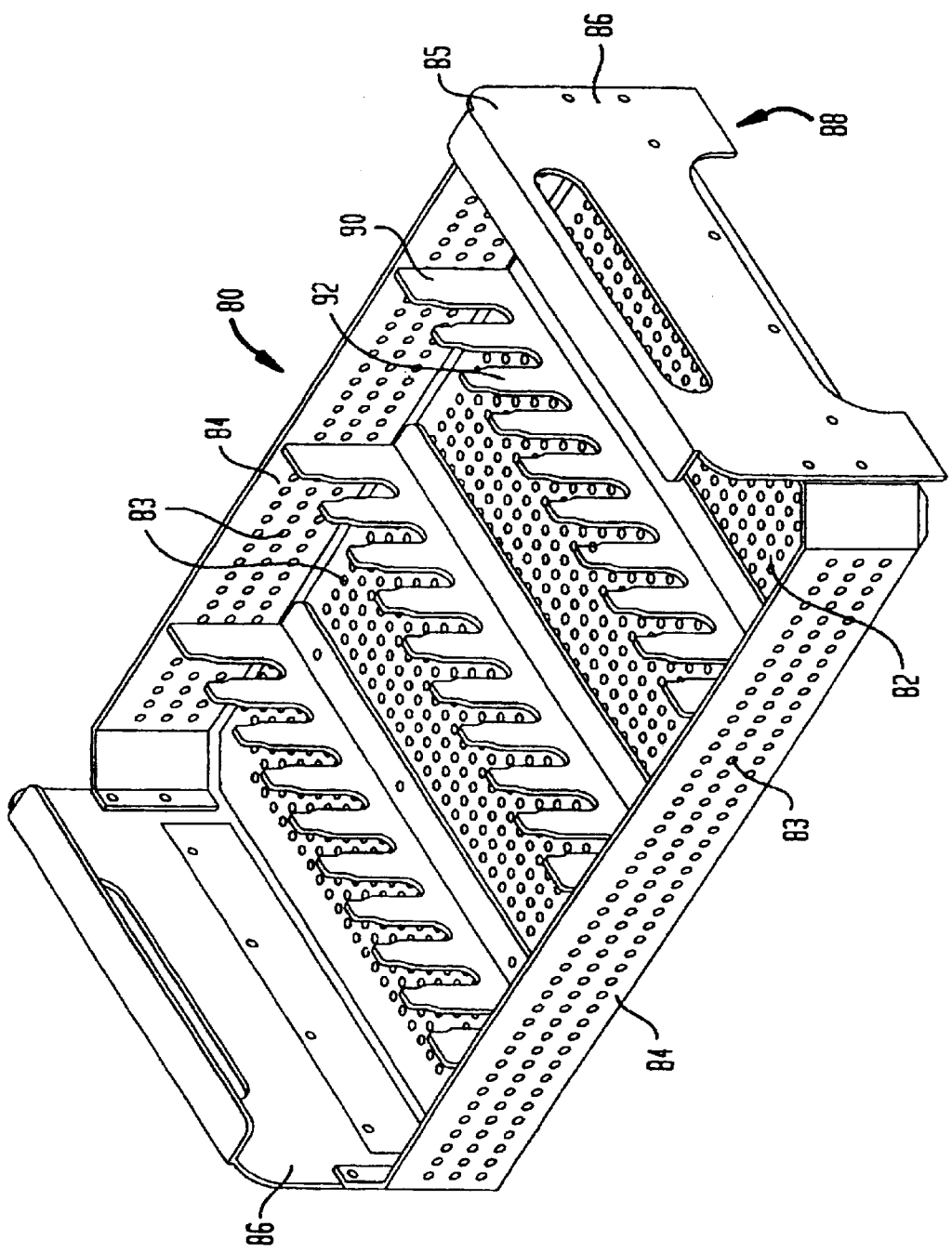
FIG. 7A is a perspective view of the preferred embodiment of the instrument limiting basket with a divider system.
Figure 7B:
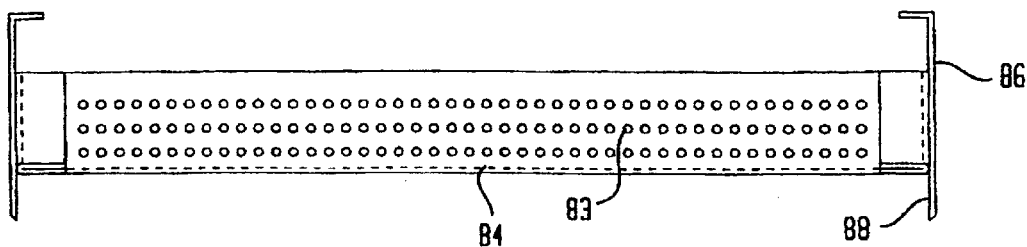
FIG. 7B is a side, elevation view of the basket with handles and feet.
Figure 7C:
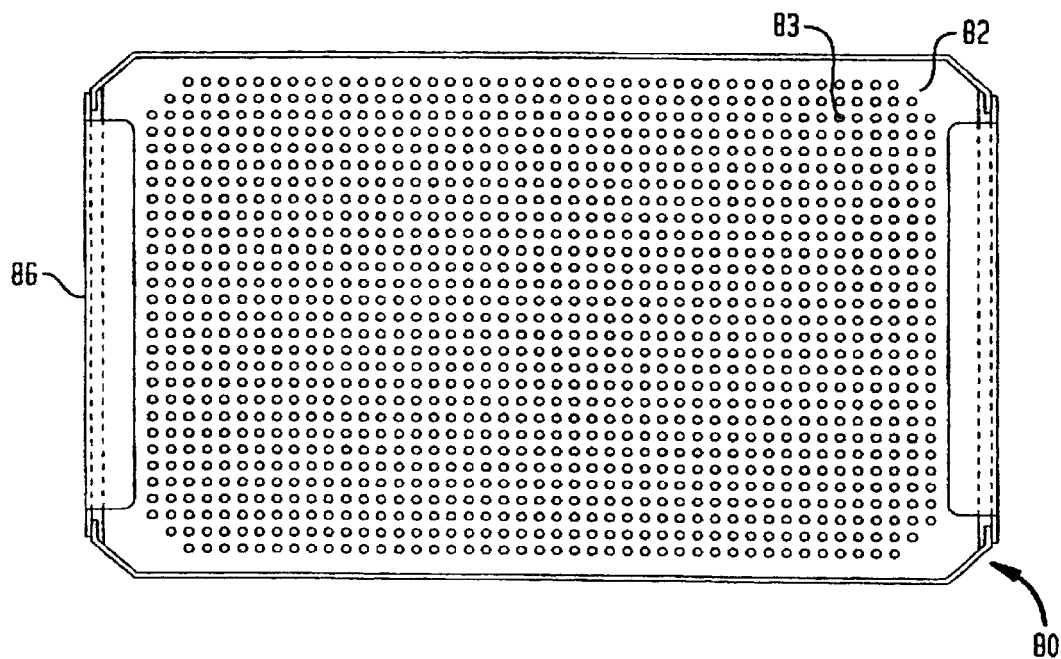
FIG. 7C is top plan view of the base of the basket with the divider system removed.
Figure 7D:
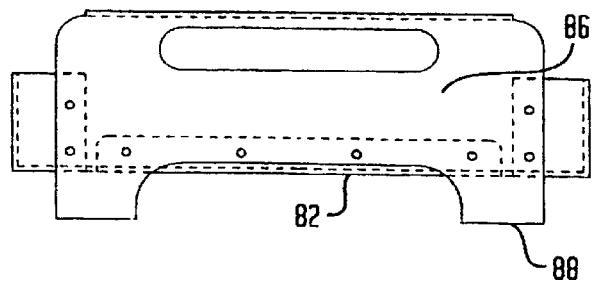
FIG. 7D is a side, elevation view of the basket handle and feet shown in FIG. 7A.

The present invention can be utilized for "stat" sterilization, for example, where immediate sterilization is required because an instrument becomes contaminated during surgery. Experimentation has shown that in order to reduce sterilization time, the amount, i.e., mass, of material to be sterilized must be limited. Limiting the amount of material to be sterilized can be accomplished by weighing the instruments. Weighing of instruments, however, is time consuming, difficult, and unreliable because the instruments are of varying masses and have odd surface areas. An improved method according to the present invention is to limit the amount of material for "stat" sterilization by utilizing a basket 80, as shown in FIG. 7A, which limits the amount of items sterilized by limiting the space in which instruments could be placed. This, in turn, limits the total mass of the instruments and guarantees that they can be sterilized sufficiently in a short period of time. Experimentation has shown that baskets which limit the volume of instruments to be sterilized to no more than twenty percent (20%) of the volume of the sterilization container allow for the most effective "stat" sterilization. In these experiments, a basket approximately 12 inches long, by 6 inches wide and 2 inches high, or a volume of approximately of 149 cubic inches, was utilized to determine the effectiveness of limiting the mass of instruments to be sterilized on a "stat" basis. The most effective use of the basket occurred in a sterilization container 18.1 inches long, by 11 inches wide and 4 inches high, or a volume of approximately 796 cubic inches.

The basket 80 of the preferred embodiment of the volume limiting present invention consists of a base 82, and two side walls 84 attached to the base 82. The base 82 and the side walls 84 are highly perforated 83. The basket 80 also contains two handle fixtures 86 on opposite sides. The handle fixtures 86 contain feet 88 extending past the base 82, and a handle portion 85 that extends beyond the side walls 84. The feet 88 and handle extend 85 beyond the sidewalls 84 so that only one basket 80 could be placed in the container.

The basket 80 may also utilize a divider system 90 to limit the amount of instruments placed in the basket 80. The divider system 90 consists of a series of brackets 92 which could be scalloped to prevent instruments from being tightly packed.

In summary, the two gas plasma alternative embodiments 100 and 200 make it possible to convert a flash sterilization container such as illustrated in FIGS. 1A through 4B into a version which is imminently acceptable and suitable for use with mid-size sterilization containers. Not only does it work with mid-size containers, it also permits sterilization to take place in approximately half the time and works especially well in a gravity displacement environment. Moreover, delicate instruments, such as cameras which cannot be sterilized with steam or ethylene oxide, can be effectively sterilized.

While the invention has been described with reference to the preferred embodiment, it will be appreciated by those of ordinary skill in the art that modifications can be made to the structure and form of the invention without departing from the spirit and scope thereof.

We claim:

1. An apparatus (80) for limiting the amount of instruments placed in a metal sterilization container (10), said apparatus (80) comprising: a metal sterilization container having a pre-determined interior volume; and a basket apparatus comprising:

a metal base (82) having a plurality of vent holes (83) located therein;

metal side walls (84) attached to said base (82), said sidewalls (84) including a plurality of vent holes (83) therein;

a pair of handle fixtures (86) located on opposite sides of said base (82), said handle fixtures (86) including feet (88) and handles (85) extending beyond said side walls (84) such that only one basket (80) can be placed in said container (10) for sterilization; and divider means (90) consisting of a series of brackets (92) attachable to said base (82), wherein the volume of said basket apparatus (80) is no more than 20% (twenty percent) of the volume of said container (10), so that all instruments in said container are thoroughly and completely sterilized.

2. The apparatus of claim 1 wherein the divider means 90 consists of a seris of brackets 92 which are scalloped.

* * * * *